United States Patent
Fiebig et al.

(10) Patent No.: US 10,206,665 B2
(45) Date of Patent: *Feb. 19, 2019

(54) BIOPSY DEVICE WITH TRANSLATING VALVE ASSEMBLY

(71) Applicant: Devicor Medical Products, Inc., Cincinnati, OH (US)

(72) Inventors: Kevin M. Fiebig, Cincinnati, OH (US); Edward A. Rhad, Fairfield, OH (US); Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 104 days.

This patent is subject to a terminal disclaimer.

(21) Appl. No.: 15/037,947

(22) PCT Filed: Nov. 24, 2014

(86) PCT No.: PCT/US2014/067106
§ 371 (c)(1),
(2) Date: May 19, 2016

(87) PCT Pub. No.: WO2015/077699
PCT Pub. Date: May 28, 2015

(65) Prior Publication Data
US 2016/0287221 A1    Oct. 6, 2016

Related U.S. Application Data

(60) Provisional application No. 61/908,399, filed on Nov. 25, 2013.

(51) Int. Cl.
*A61B 10/02* (2006.01)
(52) U.S. Cl.
CPC ...... *A61B 10/0275* (2013.01); *A61B 10/0283* (2013.01)

(58) Field of Classification Search
CPC ............. A61B 2010/0225; A61B 10/0283
See application file for complete search history.

(56) References Cited

U.S. PATENT DOCUMENTS

| | | | | |
|---|---|---|---|---|
| 4,694,821 A | * | 9/1987 | Kondo | A61B 1/12 600/158 |
| 5,145,565 A | * | 9/1992 | Kater | A61B 5/15003 204/400 |

(Continued)

FOREIGN PATENT DOCUMENTS

JP    2009-531115    9/2009

OTHER PUBLICATIONS

Chinese Office Action, Notification of First Office Action, and Search Report dated Mar. 13, 2018 for Application No. CN 201480063457.5, 10 pgs.

(Continued)

*Primary Examiner* — Sean Dougherty
(74) *Attorney, Agent, or Firm* — Frost Brown Todd LLC

(57) ABSTRACT

A biopsy device comprises a body, a needle, a cutter, and a valve assembly. The needle extends distally relative to the body. The needle defines a first lumen and a second lumen. The first and second lumens extend along a first and second longitudinal axis, respectively. The needle includes an opening fluidly coupling the first and second lumens. The cutter is translatable relative to the needle. The valve assembly comprises a vent opening and a spool body. The spool body is movable relative to the vent opening between a first and second position. The second lumen is coupled to the vent opening when the spool body is in the first position. The second lumen is sealed relative to the vent opening when the spool body is in the second position. The spool body is configured to transition between the first and second position by translation of the cutter.

19 Claims, 18 Drawing Sheets

(56) References Cited

U.S. PATENT DOCUMENTS

| | | | |
|---|---|---|---|
| 5,256,160 A * | 10/1993 | Clement | A61B 18/1482 220/502 |
| 5,526,822 A * | 6/1996 | Burbank | A61B 10/0266 600/567 |
| 6,017,316 A | 1/2000 | Ritchart et al. | |
| 6,086,544 A | 7/2000 | Hibner et al. | |
| 6,241,687 B1 * | 6/2001 | Voegele | A61B 10/0266 600/566 |
| 6,485,436 B1 * | 11/2002 | Truckai | A61B 10/0275 600/564 |
| 6,626,849 B2 | 9/2003 | Huitema et al. | |
| 6,632,182 B1 * | 10/2003 | Treat | A61B 10/04 600/564 |
| 7,204,811 B2 * | 4/2007 | Kortenbach | A61B 10/0266 600/564 |
| 7,442,171 B2 | 10/2008 | Stephens et al. | |
| 7,854,707 B2 | 12/2010 | Hibner et al. | |
| 8,038,627 B2 | 10/2011 | Hibner | |
| 8,177,729 B2 | 5/2012 | Hibner et al. | |
| 8,206,316 B2 | 6/2012 | Hibner et al. | |
| 8,529,468 B2 | 9/2013 | Hoffa et al. | |
| 8,622,926 B2 | 1/2014 | Hibner | |
| 8,801,742 B2 | 8/2014 | Rhad et al. | |
| 8,956,306 B2 | 2/2015 | Hibner | |
| 9,345,457 B2 | 5/2016 | Speeg et al. | |
| 9,638,770 B2 | 5/2017 | Dietz et al. | |
| 9,724,074 B2 | 8/2017 | Fiebig et al. | |
| 9,999,406 B2 | 6/2018 | Hibner et al. | |
| 2003/0125639 A1 * | 7/2003 | Fisher | A61B 10/0275 600/564 |
| 2003/0191413 A1 * | 10/2003 | Damarati | A61B 10/0266 600/567 |
| 2005/0159677 A1 * | 7/2005 | Shabaz | A61B 10/0275 600/567 |
| 2006/0074345 A1 | 4/2006 | Hibner | |
| 2006/0258955 A1 * | 11/2006 | Hoffman | A61B 10/06 600/564 |
| 2007/0255173 A1 * | 11/2007 | Hibner | A61B 10/0275 600/566 |
| 2009/0171242 A1 * | 7/2009 | Hibner | A61B 10/0275 600/566 |
| 2010/0152610 A1 | 6/2010 | Parihar et al. | |
| 2010/0160819 A1 | 6/2010 | Parihar et al. | |
| 2010/0292607 A1 * | 11/2010 | Moore | A61B 10/0275 600/566 |
| 2010/0317998 A1 * | 12/2010 | Hibner | A61B 10/0275 600/567 |
| 2012/0109007 A1 * | 5/2012 | Rhad | A61B 10/0275 600/567 |
| 2013/0053726 A1 * | 2/2013 | Miller | A61B 10/02 600/567 |
| 2013/0218047 A1 * | 8/2013 | Fiebig | A61B 10/0275 600/563 |

OTHER PUBLICATIONS

European Search Report, Supplementary, and Written Opinion dated Aug. 3, 2017 for Application No EP 14864195.4, 9 pgs.

International Search Report and Written Opinion dated Mar. 13, 2015 for Application No. PCT/US2014/067106, 14 pages.

Japanese Office Action, Notification of Reasons for Refusal, and Search Report dated May 25, 2017 for Application No. JP 2016-532638, 39 pgs.

Japanese Office Action, Decision to Grant a Patent, dated Jan. 18, 2018 for Application No. JP 2016-532638, 4 pgs.

Korean Office Action, Notice of Preliminary Rejection, dated Aug. 17, 2017 for Application No. KR 10-2016-2016-7013073, 10 pgs.

Korean Office Action, Decision of Patent Grant, dated Feb. 27, 2018 for Application No. KR 10-2016-7013073, 3 pgs.

U.S. Office Action, Non-Final, dated Dec. 23, 2016 for U.S. Appl. No. 14/551,685, 16 pgs.

U.S. Office Action, Notice of Allowance, dated Mar. 22, 2017 for U.S. Appl. No. 14/551,685, 8 pgs.

U.S. Appl. No. 61/908,399, filed Nov. 25, 2013.

Chinese Office Action, Notification of Second Office Action, dated Sep. 28, 2018 for Application No. CN 2014800634575, 5 pgs.

* cited by examiner

BIOPSY DEVICE WITH TRANSLATING VALVE ASSEMBLY

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; U.S. Pub. No. 2012/0109007, entitled "Handheld Biopsy Device with Needle Firing," published May 3, 2012; and U.S. Pub. No. 2012/0310110, entitled "Needle Assembly and Blade Assembly for Biopsy Device," published Dec. 6, 2012. The disclosure of each of the above-cited U.S. Pat. Nos., U.S. Patent Application Publications, and U.S. Non-Provisional Patent Applications is incorporated by reference herein.

While several systems and methods have been made and used for obtaining a biopsy sample, it is believed that no one prior to the inventors has made or used the invention described in the appended claims.

BRIEF DESCRIPTION OF THE FIGURES

While the specification concludes with claims which particularly point out and distinctly claim the biopsy device, it is believed the present biopsy device will be better understood from the following description of certain examples taken in conjunction with the accompanying drawings, in which like reference numerals identify the same elements and in which:

DETAILED DESCRIPTION

The following description of certain examples of the biopsy device should not be used to limit the scope of the present biopsy device. Other examples, features, aspects, embodiments, and advantages of the biopsy device will become apparent to those skilled in the art from the following description, which is by way of illustration, one of the best modes contemplated for carrying out the biopsy device. As will be realized, the biopsy device is capable of other different and obvious aspects, all without departing from the spirit of the biopsy device. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I. Overview of Exemplary Biopsy Device

Figure 1:
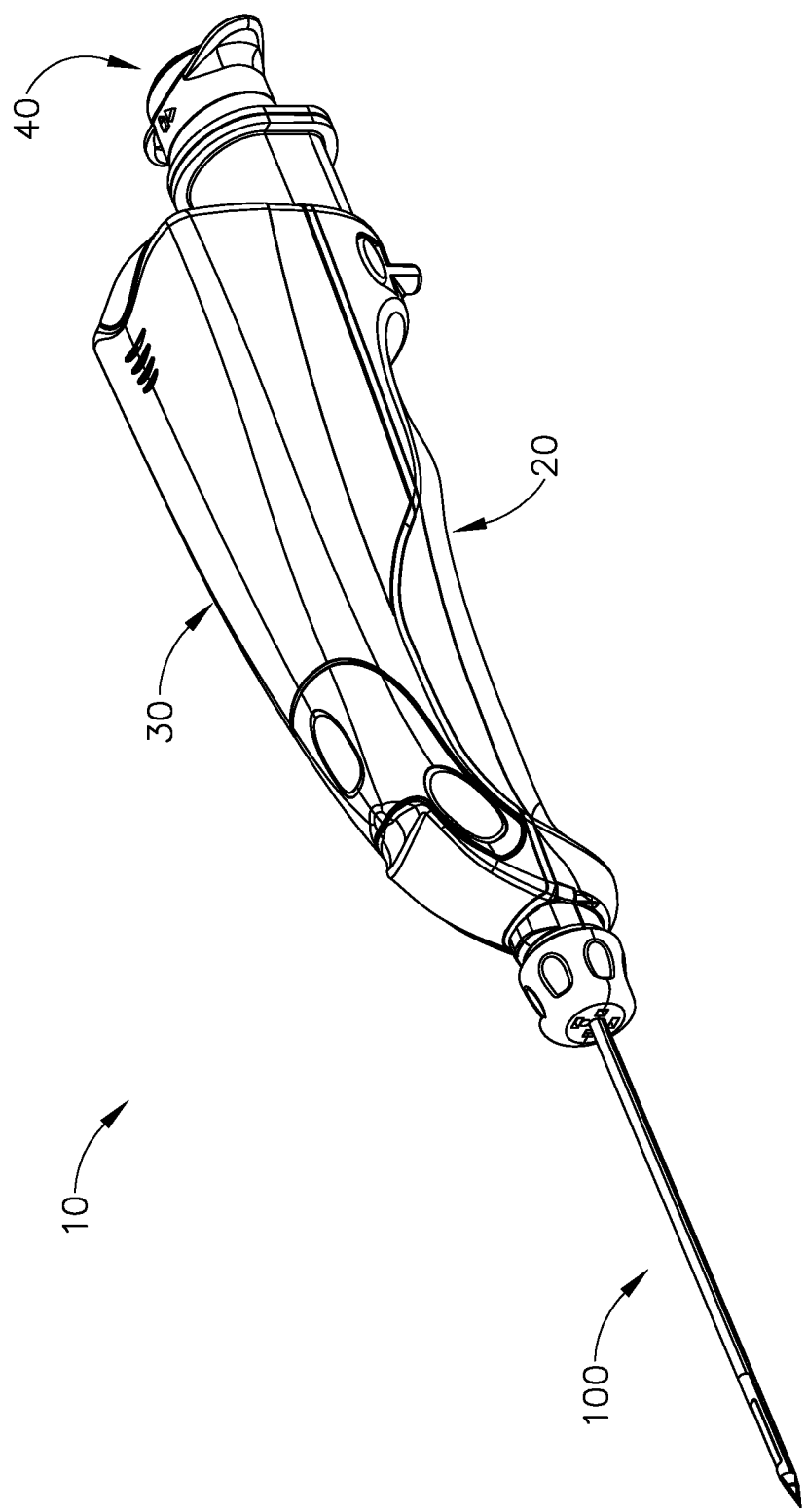
FIG. 1 depicts a perspective view of an exemplary biopsy device.
Figure 2:
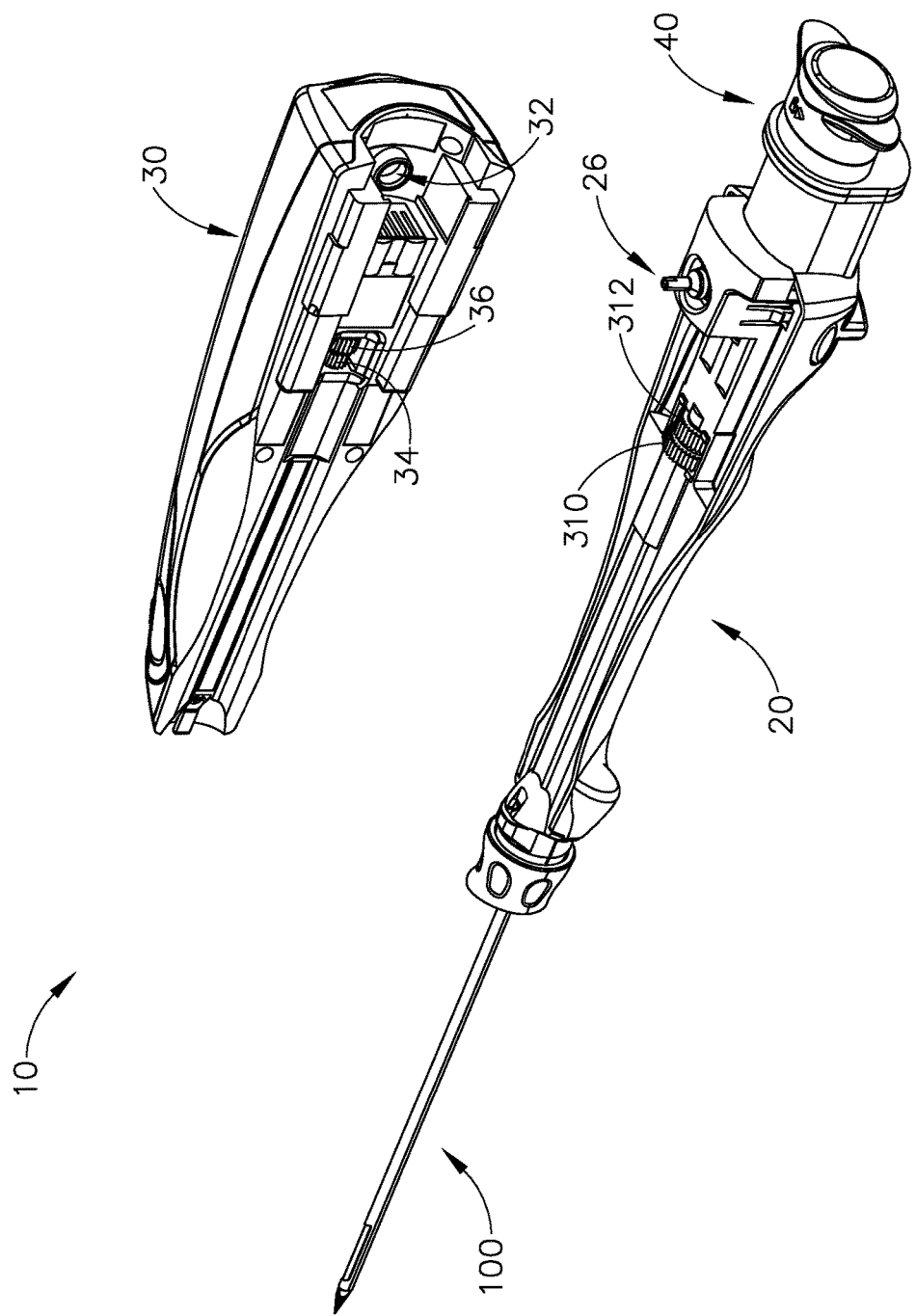
FIG. 2 depicts a perspective view of the biopsy device of FIG. 1, showing a holster detached from a probe.

FIG. 1 shows an exemplary biopsy device (10), comprising a probe (20) and a holster (30). Probe (20) comprises a needle assembly (100) that at least partially extends distally from a casing of probe (20). Needle assembly (100) is insertable into a patient's tissue to obtain tissue samples as will be described below. Biopsy device (10) further comprises a tissue sample holder (40) into which the tissue samples are deposited. By way of example only, probe (20) may be a disposable component and holster (30) may be a reusable component to which probe (20) may be coupled, as is shown in FIG. 2. Use of the term "holster" herein should not be read as requiring any portion of probe (20) to be inserted into any portion of holster (30). Indeed, in one configuration for biopsy device (10), probe (20) may simply be positioned atop holster (30). Alternatively, a portion of probe (20) may be inserted into holster (30) to secure probe (20) to holster (30). In yet another configuration, a portion of holster (30) may be inserted into probe (20). Further still, probe (20) and holster (30) may be integrally formed as a single unit.

In configurations where probe (20) and holster (30) are separable members, a port and/or a seal (32) may be provided on holster (30) to couple with a second port and/or a second seal (26) on probe (20) such that the vacuum produced by a vacuum pump (50) within holster (30) may be fluidly connected to probe (20). Holster (30) may also provide gears (34, 36) which mate to and engage with gears (310, 312) on probe (20). It should be understood that the configuration depicted in FIG. 2 that communicates vacuum and motive force between holster (30) and probe (20) is merely exemplary. In some versions, such configurations may be constructed in accordance with at least some of the teachings of U.S. Pat. No. 8,206,316 entitled "Tetherless Biopsy Device with Reusable Portion," issued Jun. 26, 2012; and/or U.S. Pub. No. 2012/0065542, entitled "Biopsy Device Tissue Sample Holder with Removable Tray," published Mar. 15, 2012, the disclosures of which are incorporated by reference herein.

With holster (30) and probe (20) connected, vacuum pump (50) can induce a vacuum within needle assembly (100) via tissue sample holder (40) and a tubular cutter (60). However, it should be understood that vacuum may be provided in other ways. For example, vacuum pump (50) may be independent of holster (30) and probe (20) and may simply be coupled by vacuum tubes to appropriate ports on biopsy device (10). Biopsy device (10) may further be configured in accordance with at least some of the teachings of U.S. Pat. No. 8,764,680, entitled "Handheld Biopsy Device with Needle Firing," issued Jul. 1, 2014; and/or U.S. Pub. No. 2012/0065542, entitled "Biopsy Device Tissue Sample Holder with Removable Tray," published Mar. 15, 2012, the disclosures of which are incorporated by reference herein. Other suitable structural and functional combinations for probe (20) and holster (30) will be apparent to one of ordinary skill in the art in view of the teachings herein.

II. Exemplary Holster

Figure 3:
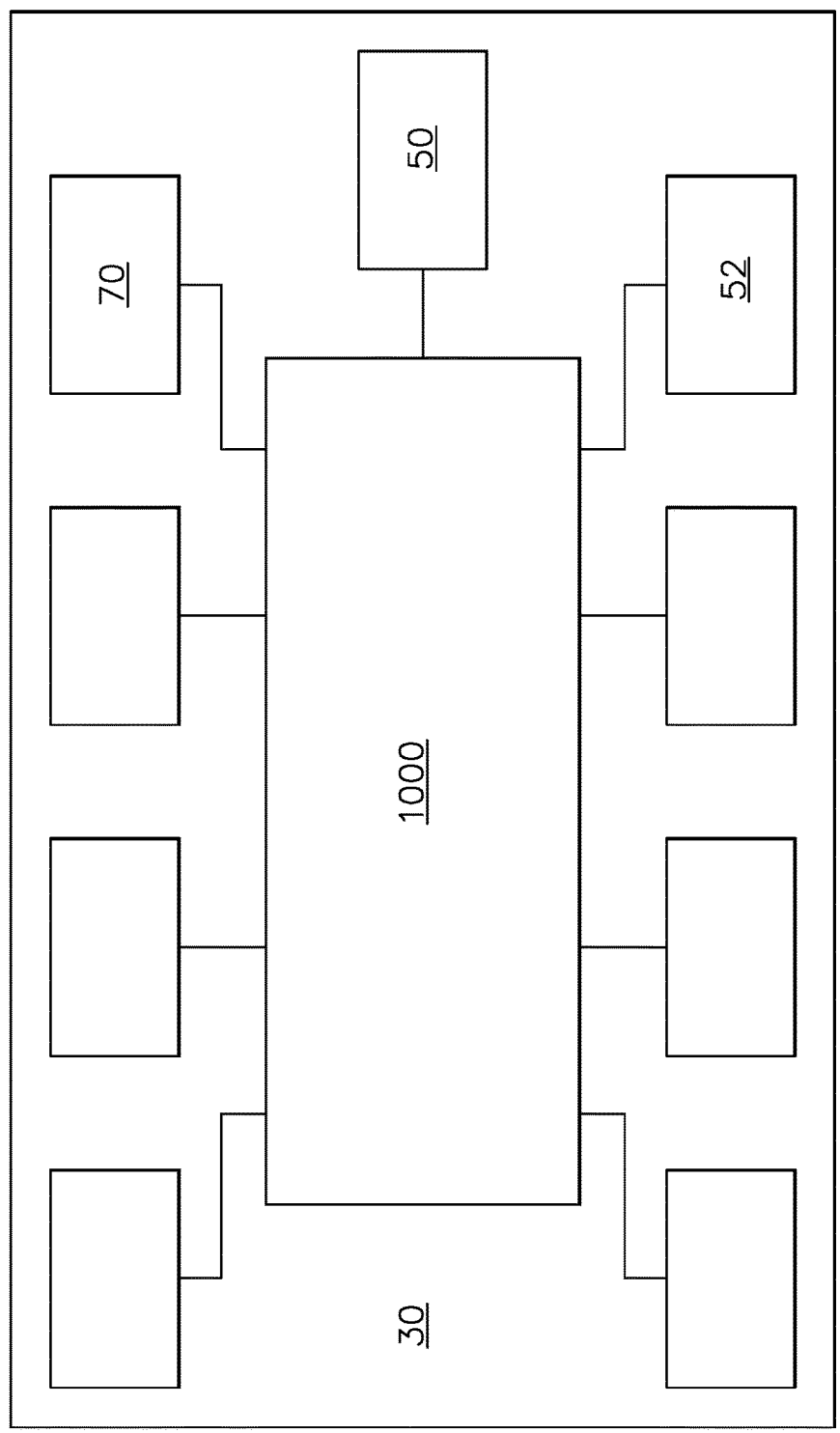
FIG. 3 depicts a schematic view of exemplary electrical and/or electromechanical components of the holster of FIG. 2.

Holster (30), shown schematically in FIG. 3, comprises vacuum pump (50), a motor (70), a control module (1000), a vacuum sensor (52), and any other suitable electrical and/or electromechanical components. Vacuum pump (50) of the present example comprises a conventional diaphragm pump that is mechanically coupled to motor (70). Vacuum sensor (52) is coupled to vacuum pump (50) or along any vacuum path therefrom such that vacuum sensor (52) can determine the level of vacuum created by vacuum pump (50). Vacuum sensor (52) is electrically coupled to control module (1000) so that vacuum sensor (52) may output signals indicative of the vacuum level to control module (1000). In the configuration shown, motor (70) is operable to translate and/or rotate cutter (60), as will be described below, and to activate vacuum pump (50), though this is merely optional and a second motor (not shown) may be provided to run vacuum pump (50). In particular, motor may be coupled to a cutter drive assembly (not shown). Such a cutter drive assembly (not shown) may rotate gears (34, 36) simultaneously. As noted above, gears (34, 36) mesh with gears (310, 312) in probe (20) thus allowing motor (70) to translate and/or rotate cutter (60). Other various configurations for holster (30) may be provided as will be apparent to one of ordinary skill in the art in view of the teachings herein. By way of example only, the cutter drive assembly (not shown) and/or other features of holster (30) may be constructed in accordance with at least some of the teachings of U.S. Pat. No. 8,206,316 entitled "Tetherless Biopsy Device with Reusable Portion," issued Jun. 26, 2012; and/or U.S. Pat. No. 8,764,680, entitled "Handheld Biopsy Device with Needle Firing," issued Jul. 1, 2014, the disclosures of which are incorporated by reference herein.

III. Exemplary Probe

Figure 4:
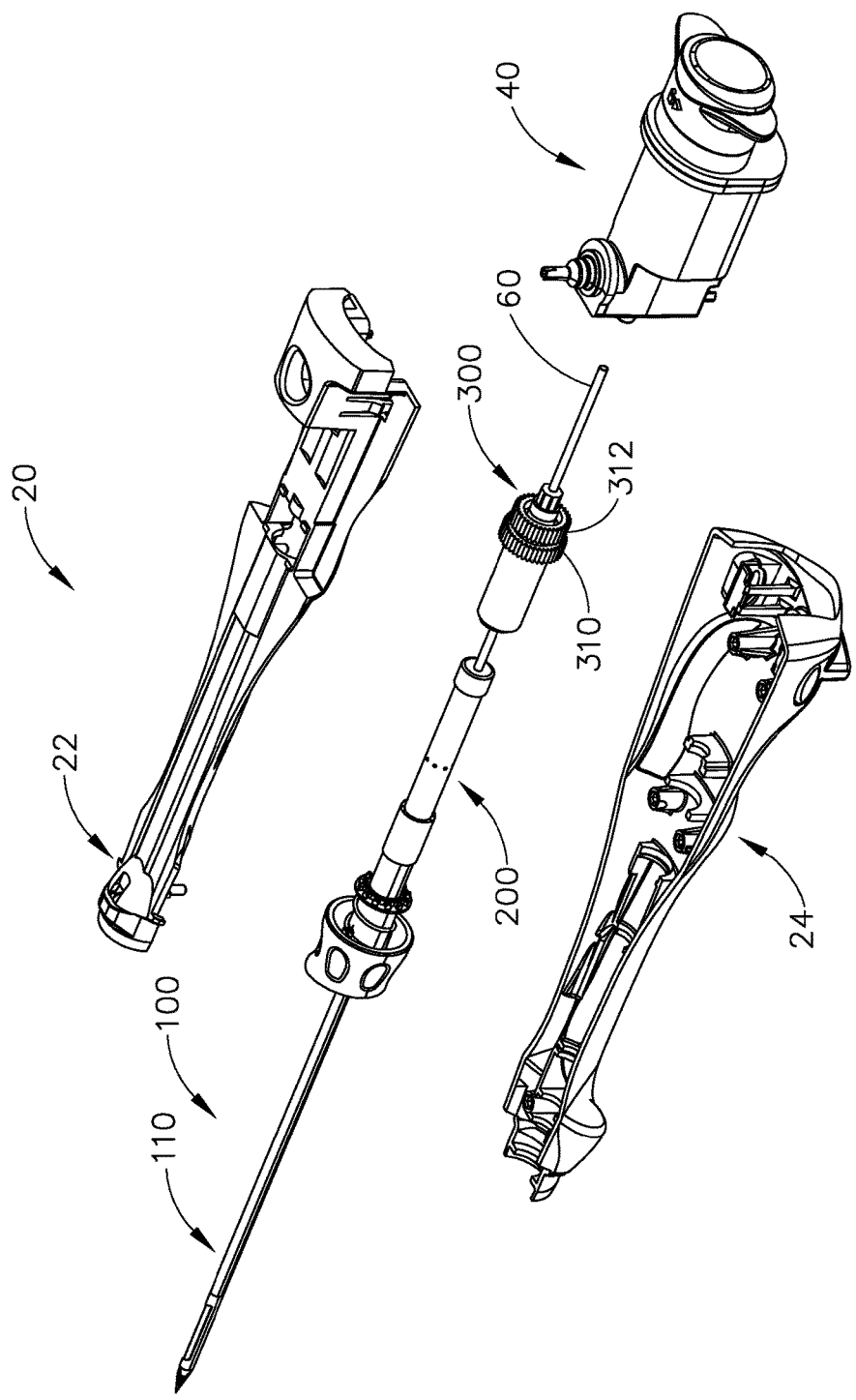
FIG. 4 depicts an exploded perspective view of the probe of FIG. 2.

FIG. 4 depicts a partially exploded view of probe (20) showing needle assembly (100), a cutter actuation assembly (300), a probe housing (22, 24) and tissue sample holder (40). Needle assembly (100) comprises a needle portion (110) and a valve assembly (200). As will be described in greater detail below, needle assembly (100) is generally operable to pierce tissue where cutter (60) can be positioned to sever a tissue sample from a patient and transport the tissue sample to tissue sample holder (40). More specifically, the needle portion (110) of needle assembly (100) is inserted into a patient's tissue. Cutter actuation assembly (300) is then operable to selectively actuate cutter (60) to an open position. Once cutter (60) is actuated by cutter actuation assembly (300) into an open position, tissue may be prolapsed into needle portion (110) by means of a vacuum communicated through cutter (60). Cutter (60) may then be selectively actuated by means of cutter actuation assembly (300) into the closed position, severing the prolapsed tissue from the patient. Vent assembly (300) is then operable to selectively vent a portion of needle portion (110) to atmosphere thus creating a pressure differential between proximal and distal ends of the prolapsed tissue. The pressure differential then transports the prolapsed tissue through cutter (60) to tissue sample holder (40).

A. Exemplary Cutter Actuation Assembly

Cutter actuation assembly (300) comprises a series of gears (310, 312). Gears (310, 312) are configured to translate and/or rotate cutter (60). In the configuration shown, gears (310, 312) are coupled to motor (70) when probe (20) is attached to holster (30). In particular, two gears (310, 312) are controlled by motor (70) such that one gear (310) translates cutter (60) and another gear (312) rotates cutter (60) simultaneously. Other configurations may be provided utilizing different gear (310) arrangements. Moreover, configurations involving additional motors (70) may be used. Various suitable motor (70) and gear (310, 312) combinations will be apparent to one of ordinary skill in the art in view of the teachings herein. Indeed, cutter actuation assembly (300) may be constructed in accordance with at least some of the teachings of U.S. Pat. No. 8,206,316, entitled "Tetherless Biopsy Device with Reusable Portion," issued Jun. 26, 2012, the disclosure of which is incorporated by reference herein.

B. Exemplary Needle Portion

Figure 5:
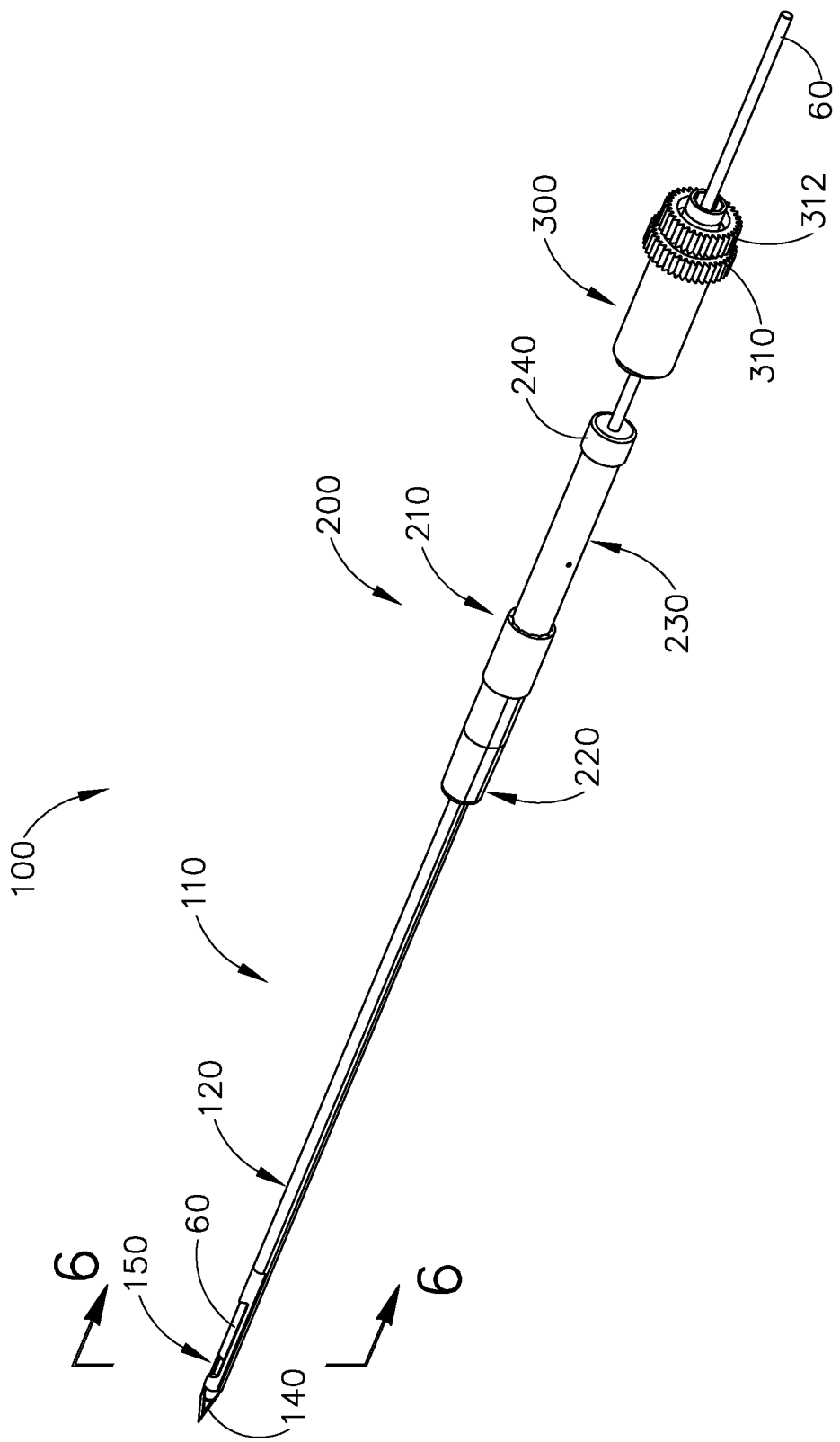
FIG. 5 depicts a perspective view of an exemplary needle assembly and associated components of the probe of FIG. 2.
Figure 6:
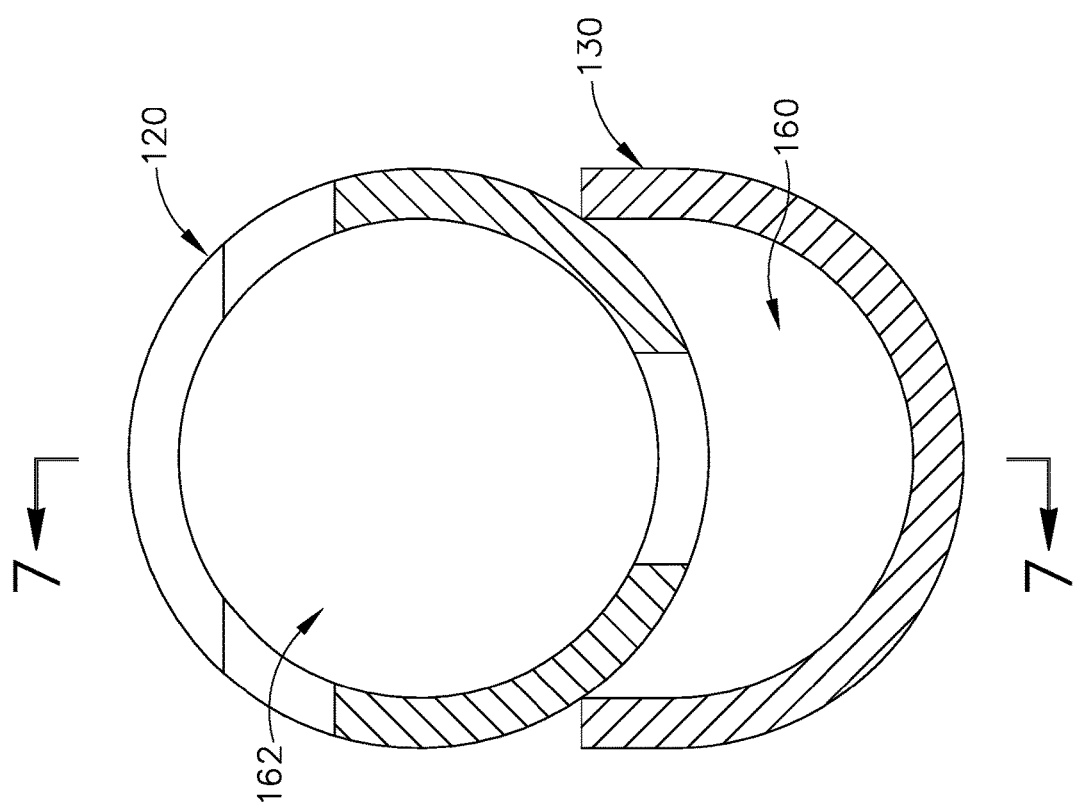
FIG. 6 depicts a cross-sectional view of the needle assembly of FIG. 5, taken along line 6-6 of FIG. 5.

FIGS. 5 through 7 show an exemplary needle portion (110). Needle portion (110) comprises a cannula (120), a partial cannula (130), a tissue piercing tip (140), and a lateral aperture (150). As is shown, cannula (120) is positioned on top of partial cannula (130). Cannula (120) and partial cannula (130) define a first lumen portion (160) and a second lumen portion (162). As is best seen in FIG. 6, cannula (120) is generally circular in shape while partial cannula (130) is semi-circular. Cannula (120) and partial cannula (130) may be coextensive with their proximal end terminating within the valve assembly (200) and their distal end supporting tissue piercing tip (140). Although needle portion (110) is shown as having a generally ovular cross-section, it should be understood that other cross-sectional shapes may be used. Indeed, needle portion (110) may be comprised of only circular tubes thus creating a generally figure eight cross-section. Alternatively, needle portion (110) may be comprised of two square tubes thus creating a generally square cross-section. Yet in other configurations, any other suitable shape may be used.

Figure 7A:
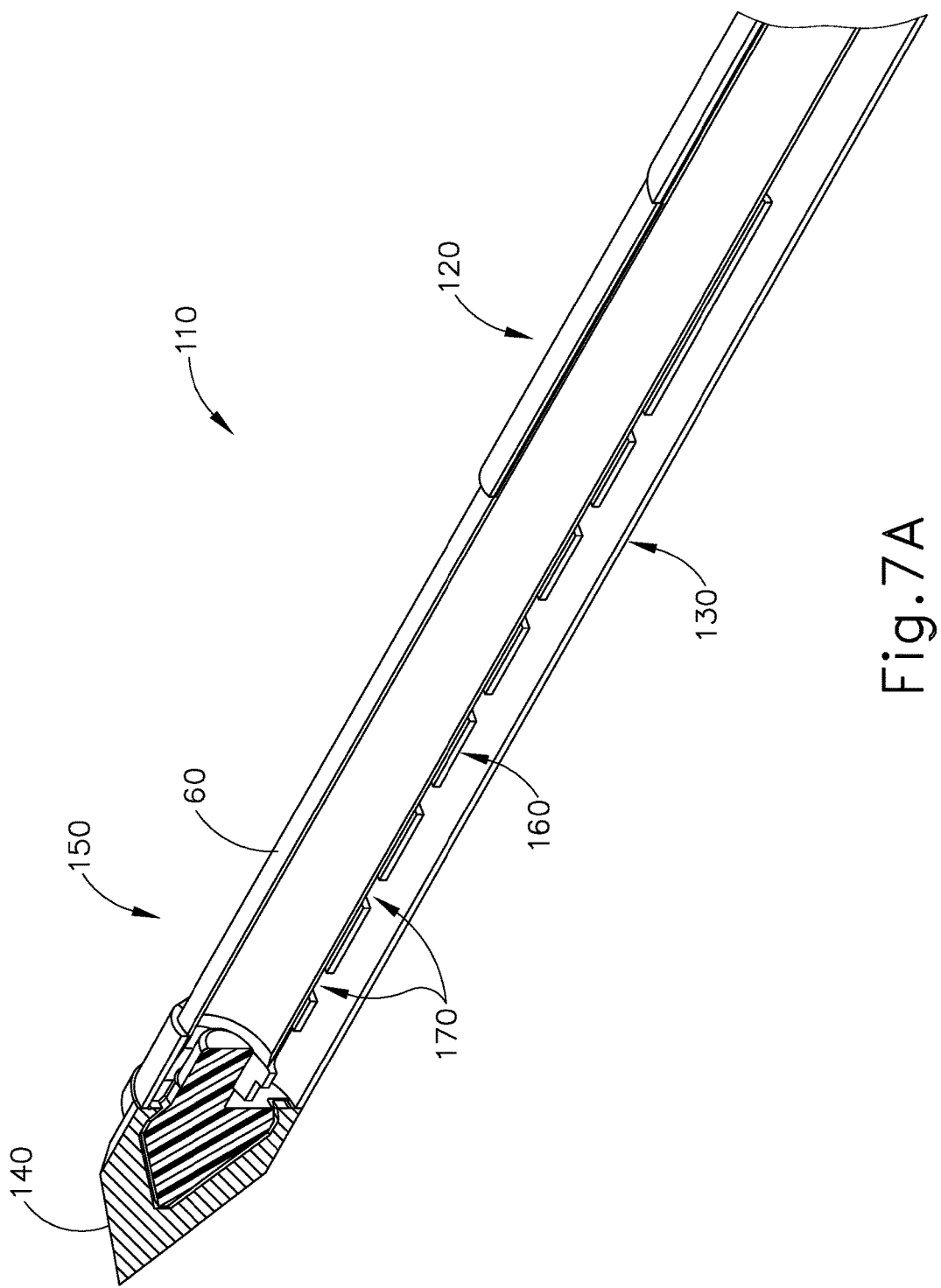
FIG. 7A depicts a cross-sectional perspective view of the distal end of the needle assembly of FIG. 5, taken along line 7-7 of FIG. 6, showing the cutter in a closed position.
Figure 7B:
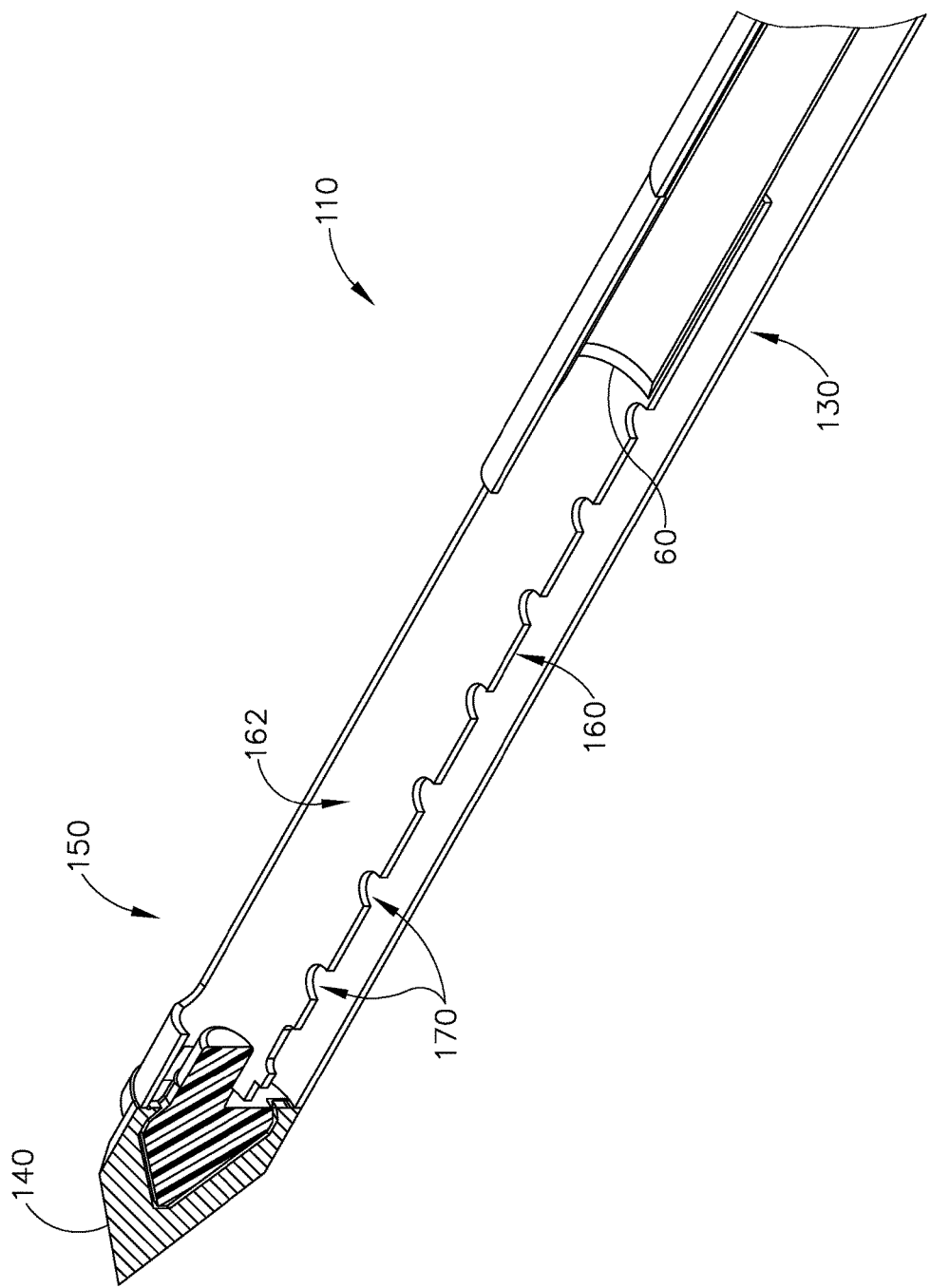
FIG. 7B depicts a cross-sectional perspective view of the distal end of the needle assembly of FIG. 5, taken along line 7-7 of FIG. 6, showing the cutter in an open position.
Figure 7C:
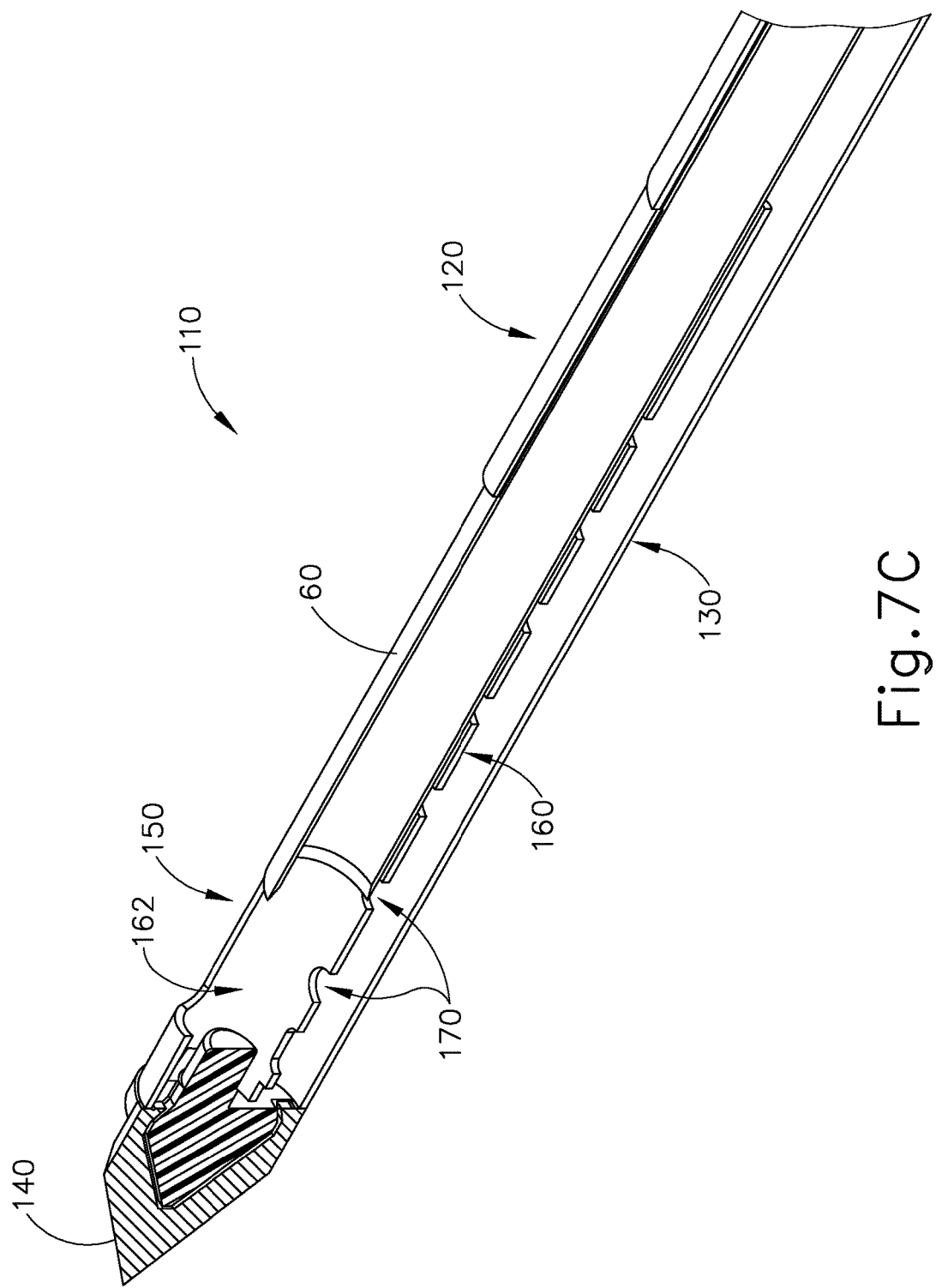
FIG. 7C depicts a cross-sectional perspective view of the distal end of the needle assembly of FIG. 5, taken along line 7-7 of FIG. 6, showing the cutter in a partially open position.

FIGS. 7A to 7C depict needle portion (110) with cutter (60) in various states. In particular, cannula (120) is configured to receive cutter (60) and to permit cutter (60) to translate and rotate within second lumen portion (162). Cannula (120) further comprises lateral aperture (150). Lateral aperture (150) is sized to receive prolapsed tissue during operation of biopsy device (10). The sidewall of cannula (120) opposite lateral aperture (150) comprises a plurality of openings (170) that provide fluid communication between first lumen portion (160) and second lumen portion (162). In the present example, first lumen portion (160) may selectively provide atmospheric air to vent second lumen portion (162) through the plurality of openings (170). Such an atmospheric vent in second lumen portion (162) allows severed tissue to be drawn through cutter (60) and into tissue sample holder (40) under the influence of vacuum from vacuum pump (50).

The series depicted in FIGS. 7A through 7C shows cutter (60) first in a closed position, then in an open position and finally in an intermediate position. Each position depicted may correspond to a particular stage in the tissue sample extraction process. For example, as depicted in FIG. 7A, the cannula (120) may penetrate a patient's tissue when cutter (60) is in a closed position. In the closed position, cutter (60) is in its furthest distal position relative to lateral aperture (150). Thus, cannula (120) may penetrate through tissue smoothly without catching any surrounding tissue that might impede penetration.

FIG. 7B depicts cutter (60) in the open position, where cutter (60) is in its furthest proximal position relative to lateral aperture (150). This state may, for example, correspond to a position where cannula (120) is oriented inside a patient where a tissue sample may be taken. With cutter (60) in its furthest proximal position relative to lateral aperture (150) a vacuum may be applied to prolapse patient's tissue through lateral aperture (150).

Finally, FIG. 7C depicts cutter (60) in the intermediate position, where cutter (60) is in a position between its furthest distal and proximal positions relative to lateral aperture (150). In this position, cutter (60) may be in a motive state from either a closed position or an open position to a closed or open position, respectively. For example, cutter (60) may move from an open to closed position so that cutter (60) may sever a tissue sample. Alternatively, cutter may move from a closed to open position in order to allow the patient's tissue to prolapse through lateral aperture (150). As will be described in further detail below, these various positions correspond to various pneumatic states of valve assembly (200). It should be understood that the various positions of cutter (60) and the corresponding stages in the tissue extraction process are merely exemplary and other suitable combinations will be apparent to one of ordinary skill in the art from the teachings herein.

Tissue piercing tip (140) is shown as having a generally conical body with a flat blade protruding therefrom. The shape of tissue piercing tip (140) is merely exemplary and many other suitable shapes may be used. For example, tissue piercing tip (140) may be in the shape of a blade protruding from needle portion (110), disregarding the conical body. Still in further variations, the tissue piercing tip (140) may have a flat blade portion of varying shapes and configurations. Other various configurations for tissue piercing tip (140) and for needle portion (110) in general may be provided as will be apparent to one of ordinary skill in the art in view of the teachings herein. By way of example only, needle portion (110) may be constructed in accordance with at least some of the teachings of U.S. Pat. No. 8,801,742, entitled "Needle Assembly and Blade Assembly for Biopsy Device," issued Aug. 8, 2014, the disclosure of which is incorporated by reference herein.

C. Exemplary Valve Assembly

Figure 8:
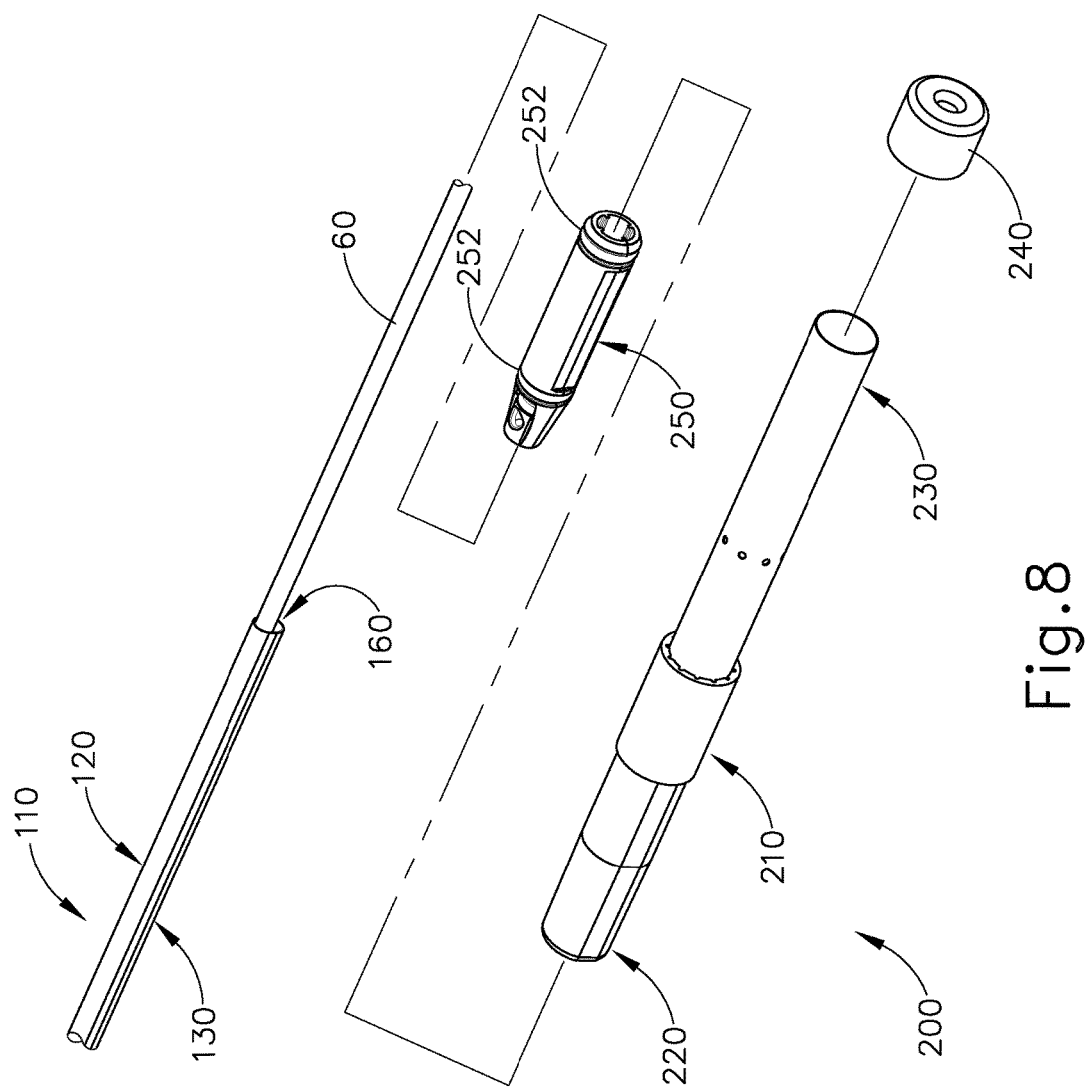
FIG. 8 depicts an exploded perspective view of the needle assembly of FIG. 5.
Figure 9:
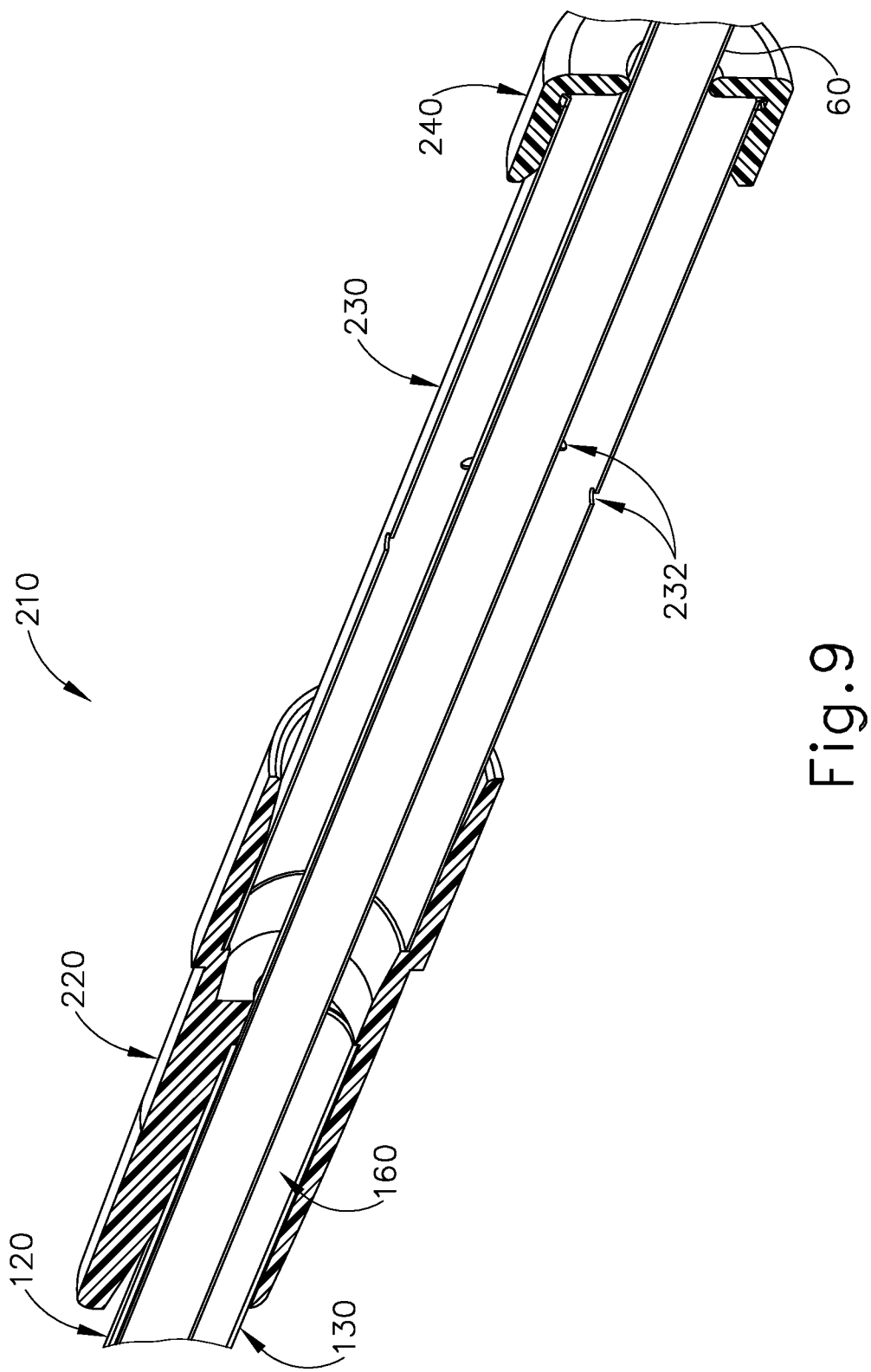
FIG. 9 depicts a side cross-sectional perspective view of valve components of the needle assembly of FIG. 5.

FIG. 8 depicts an exploded view of an exemplary valve assembly (200). Valve assembly (200) comprises a manifold (210), a static seal (240) and a spool body (250). Manifold (210) couples valve assembly (200) to the proximal end of needle portion (110) of needle assembly (100). In particular, manifold (210) comprises a needle coupling end (220) and a venting end (230). As is best seen in FIG. 9, needle coupling end (220) of manifold (210) is configured to receive the proximal end of needle portion (110) of needle assembly (100). In the present example, the coupling is made at the termination of cannula (120) and partial cannula (130). Cutter (60) then continues through valve assembly (200) to tissue sample holder (40). As will be described in more detail below, needle coupling end (220) creates an air tight seal around cannula (120) and partial cannula (130) to permit fluid flow from venting end (230) through first lumen portion (160). Coupling between needle portion (110) and needle coupling end (220) of manifold (210) may be facilitated by any suitable means such as adhesive bonding, a resilient sealing feature, an interference fitting, or a mechanical fastening means.

FIG. 9 shows venting end (230) of manifold (210) in position around cutter (60). Spool body (250) is not shown in FIG. 9 so that the details of venting end (230) may be visible. Venting end (230) extends proximally from needle coupling end (220). In the present example, needle coupling end (220) and venting end (230) are integrally formed as a single unit. In other examples, needle coupling end (220) and venting end (230) may be separate components joined together by any suitable fastening means. Venting end (230) terminates at the proximal end of manifold (210) where static seal (240) is affixed thereto. Venting end (230) defines a plurality of transverse openings (232) that are longitudinally co-located with each other. Transverse openings (232) are equidistantly spaced from each other about the outer perimeter of venting end (230) at their common longitudinal position. As will be described in greater detail below, transverse openings (232) provide communication of atmospheric air to the interior of venting end (230) such that atmospheric air can be fluidly communicated to first lumen portion (160).

Static seal (240) is affixed to the proximal end of manifold (210). Cutter (60) extends through static seal (240). Although cutter (60) is free to rotate and translate through static seal (240), static seal (240) prevents fluid communication at the interface between cutter (60) and static seal (240). Thus, with the seal created by static seal (240) and the seal created by needle coupling end (220), flow of atmospheric air can be limited to transverse openings (232) to first lumen portion (160). Static seal (240) is shown as a separate component of valve assembly (200). This allows spool body (250) to be inserted into manifold (210). It should be understood, however, that static seal (240) may be integrally formed with manifold (210). This may be the case particularly if manifold (210) is comprised of more than one component rather than the unitary design that is shown.

Figure 10:
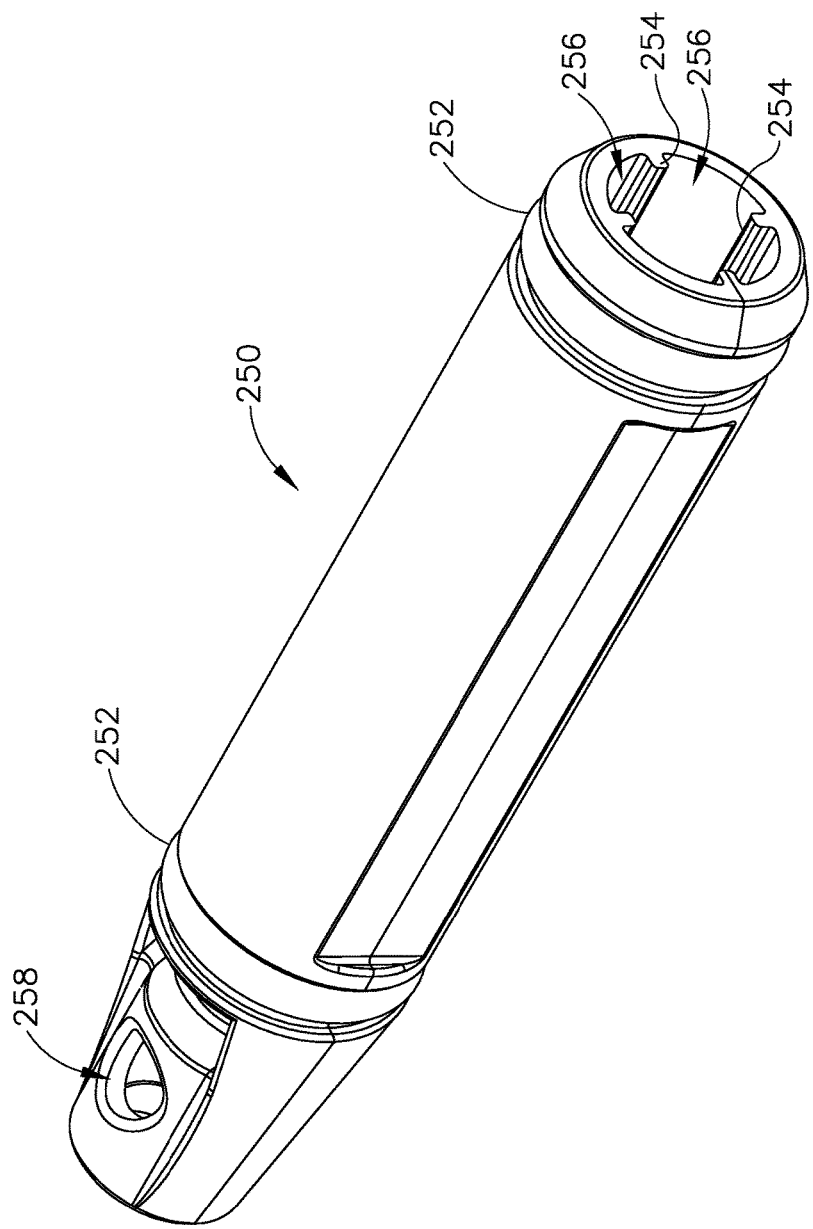
FIG. 10 depicts a perspective view of a spool body of the valve components of FIG. 9, oriented with a distal end facing away.
Figure 11:
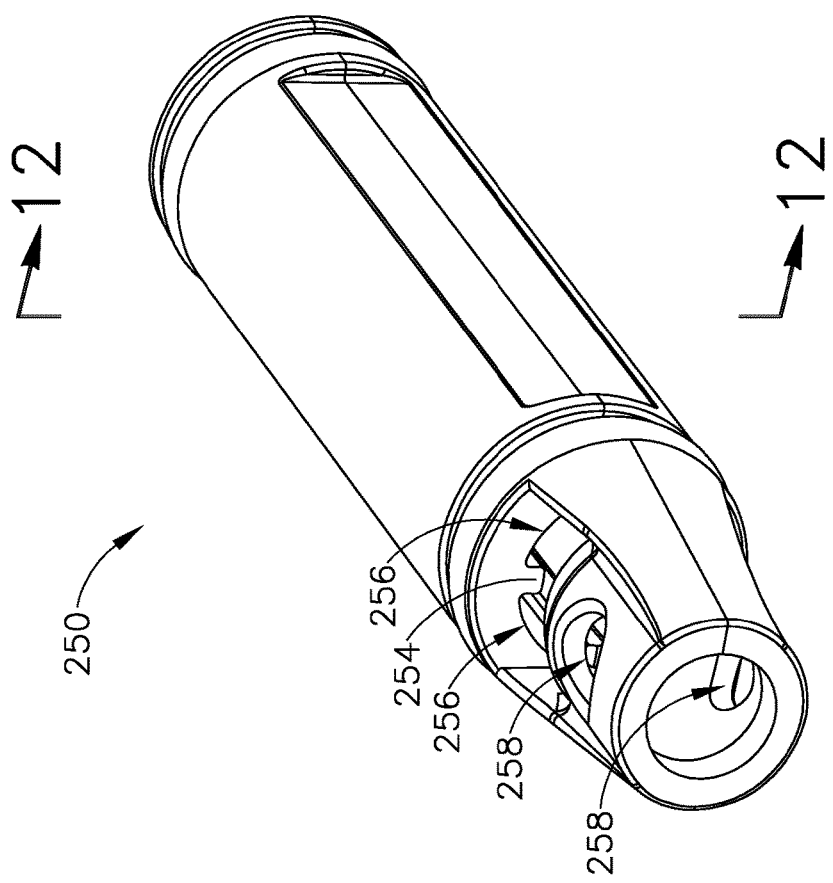
FIG. 11 depicts a perspective view of the spool body of FIG. 10, oriented with a proximal end facing away.
Figure 12:
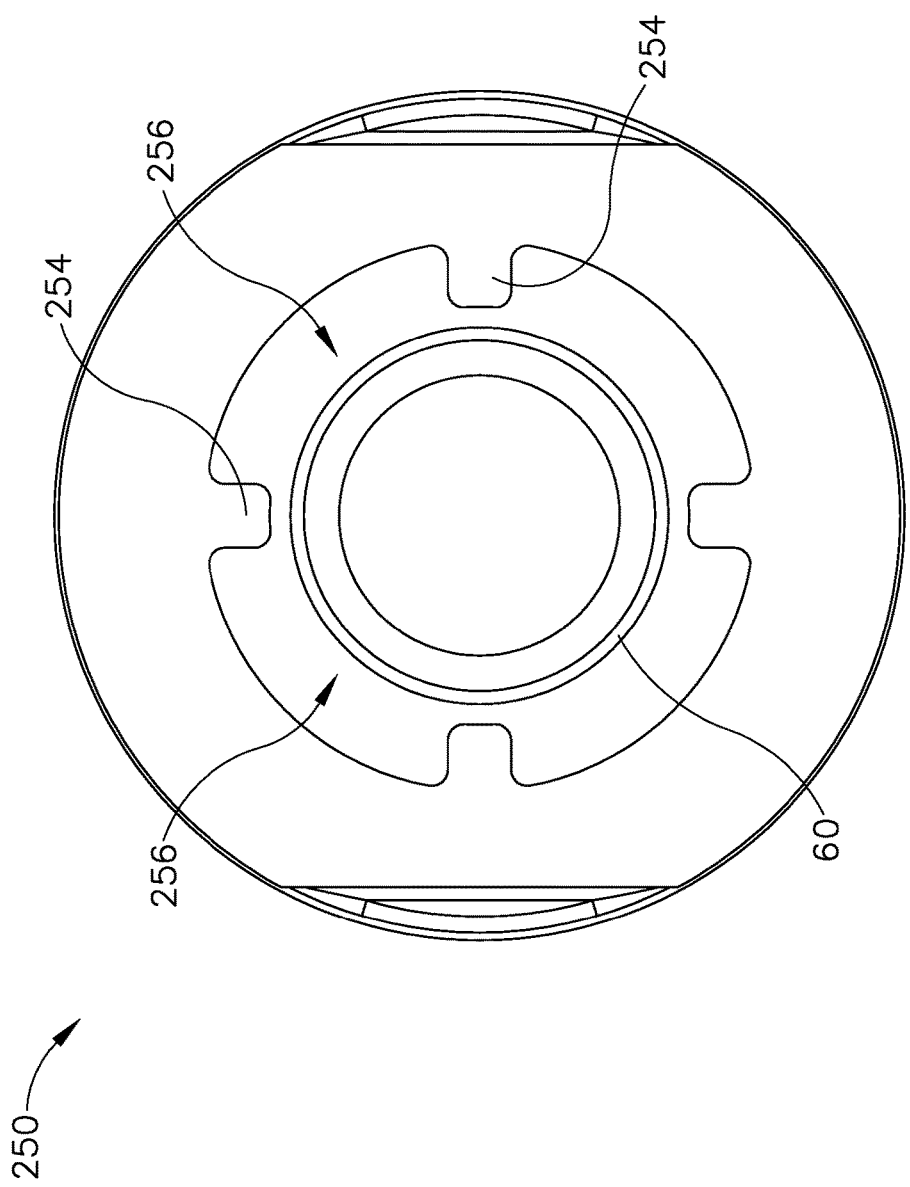
FIG. 12 depicts a cross-sectional view of the spool body of FIG. 10, taken along line 12-12 of FIG. 11.

FIGS. 10 through 12 provide detailed views of spool body (250). Spool body (250) has o-rings (252) situated near the distal end and proximal end of spool body (250). As will be described in more detail below, o-rings (252) create a seal between spool body (250) and the inner diameter surface of venting end (230) of manifold (210). Although spool body (250) is shown with two o-rings (252), any suitable number of o-rings may be utilized.

Spool body (250) is shown as generally hollow with inwardly extending cutter engaging members (254) defining venting channels (256). As can best be seen in FIG. 12, cutter engaging members (254) allow spool body (250) to be positioned on cutter (60), coaxially with cutter (60). In the present example, there are four cutter engaging members (254) oriented equidistantly around the interior of spool body (250). Alternatively, spool body (250) may be comprised of any suitable number of cutter engaging members (254). Cutter engaging members (254) extend longitudinally from the proximal end of spool body (250) toward the distal end of spool body (250). It should be understood that the longitudinal extension of cutter engaging members (254) is merely exemplary and other configurations may be used. For instance, cutter engaging members (254) may extend for only a portion of spool body (250). In yet another configuration, cutter engaging members (254) may have a break in their longitudinal extension whereby they extend for a portion of spool body (250), stop, then continue for another portion.

Venting channels (256) permit fluid communication between the outer diameter of cutter (60) and the inner diameter of spool body (250) from the proximal end of spool body (250) to the distal end of spool body (250). In the present example, four venting channels (256) are defined by the four cutter engaging members (254). However, it should be understood that any alternative configuration of cutter engaging members (254) may provide a corresponding alternative configuration of venting channels (256). Various other alternative configurations of cutter engaging members (254) and venting channels (256) will be apparent to one of ordinary skill in the art in view of the teachings herein.

The distal end of spool body (250) includes cutter securing holes (258) which permit spool body (250) to be affixed to cutter (60) via set screws or some other suitable type of fastening member. Accordingly, spool body (250) may rotate and translate as cutter (60) translates and rotates. Two cutter securing holes (258) are shown. It should be understood that any suitable number of cutter securing holes (258) may be used. Further still, cutter securing holes (258) may even be omitted entirely and replaced with some other means of securing spool body (250) to cutter (60) as will be apparent to one of ordinary skill in the art in light of the teachings herein.

IV. Exemplary Pneumatic States

Figure 13A:
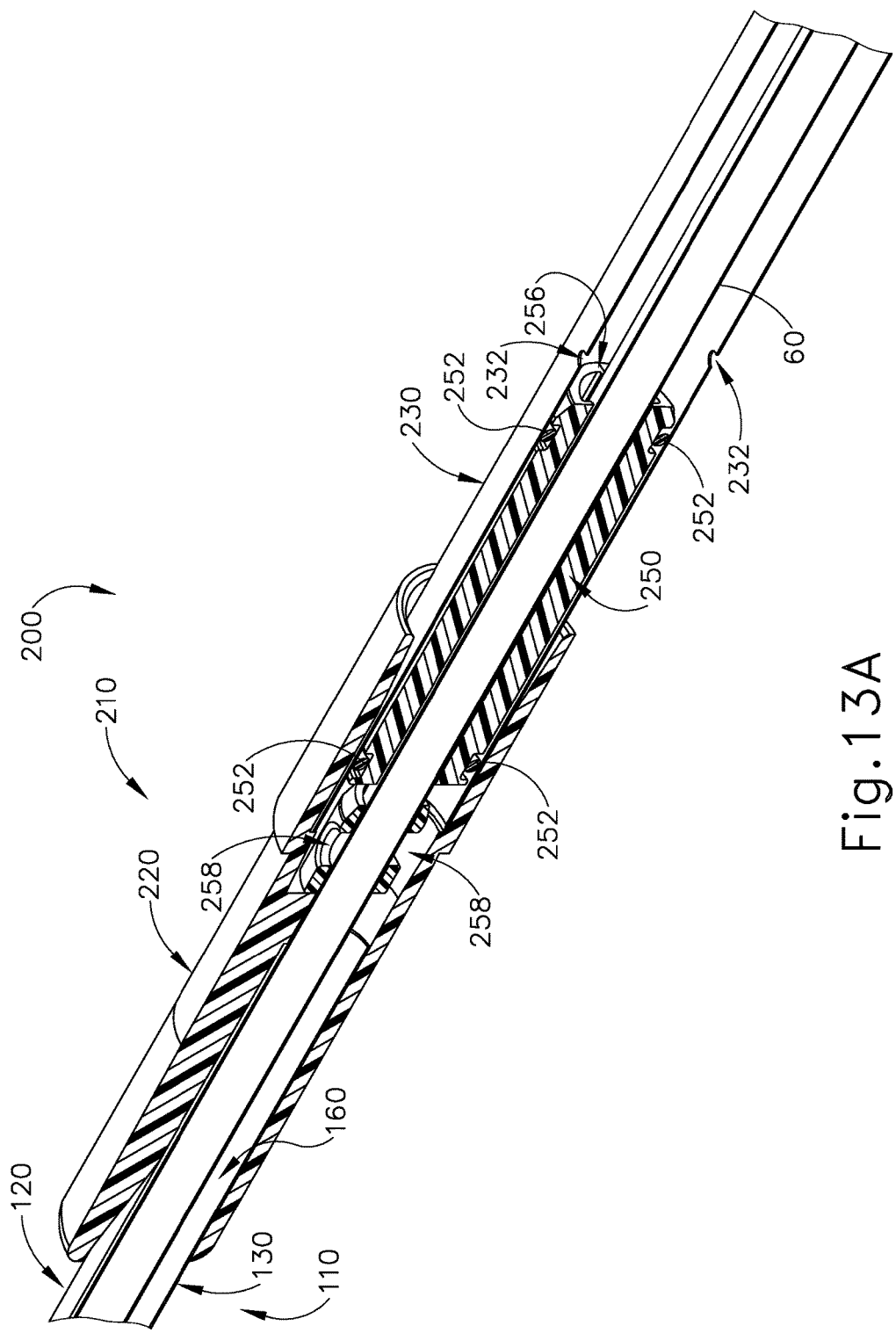
FIG. 13A depicts a cross-sectional perspective view taken along the side of the exemplary needle assembly showing the cutter and the valve assembly in a venting position corresponding to the closed cutter position depicted in FIG. 7A.
Figure 13B:
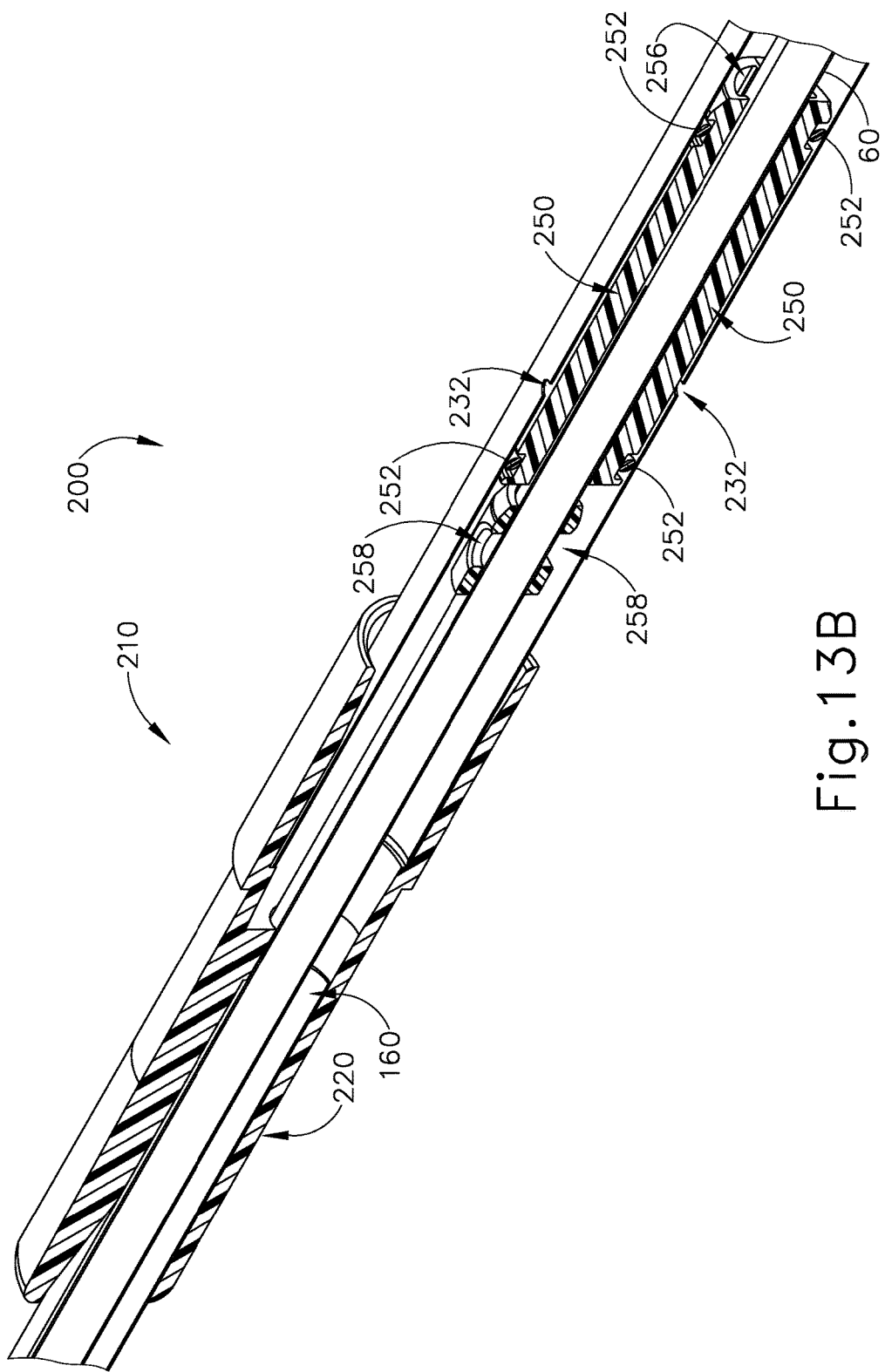
FIG. 13B depicts a cross-sectional perspective view taken along the side of the exemplary needle assembly showing the cutter and the valve assembly in a first non-venting position corresponding to the opened cutter position depicted in FIG. 7B.
Figure 13C:
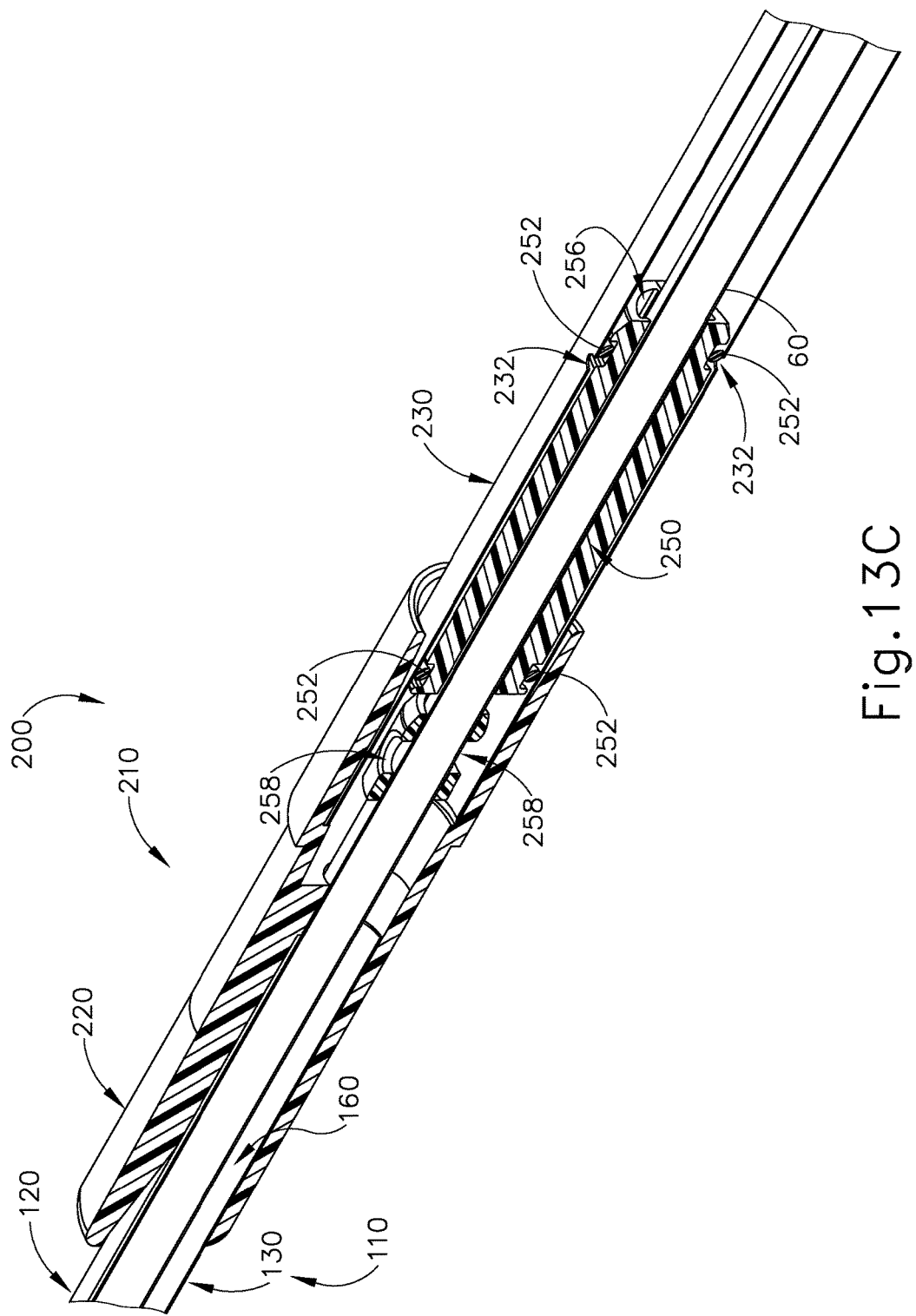
FIG. 13C depicts a cross-sectional perspective view taken along the side of the exemplary needle assembly showing the cutter and the valve assembly in a second non-venting position corresponding to the partially opened cutter position depicted in FIG. 7C.

FIGS. 13A to 13C show spool body (250) in various exemplary pneumatic states. In FIG. 13A, spool body (250) is shown in a venting state. In the venting state spool body (250) is in its furthest distal position relative to manifold (210). As was described above, spool body (250) is attached to cutter (60). Accordingly, the venting state corresponds to cutter (60) being in its furthest distal position relative to lateral aperture (150), as can be seen in FIG. 7A. When spool body (250) is positioned in its furthest distal position relative to manifold (210), transverse openings (232) permit fluid communication of atmospheric air through venting channels (256) in spool body (250) to first lumen portion (160). In particular, the proximal most o-ring (252) is distal to transverse openings (232). Spool body (250) thus provides a clear fluid path between transverse openings (232) and venting channels (256). Fluid communication of atmospheric air to first lumen portion (160) correspondingly allows negative pressure to exist behind a severed tissue sample inside cutter (60) at the distal end of cutter (60). Accordingly, when a vacuum is applied to cutter (60) a severed tissue sample may be transported proximally through cutter (60) to tissue sample holder (40).

FIG. 13B depicts spool body (250) in a non-venting state. In the non-venting state, spool body (250) is in its furthest proximal portion relative to manifold (210). In the furthest proximal position, spool body (250) is positioned to seal transverse openings (232) in venting end (230) of manifold (210). In particular, transverse openings (232) are disposed between spool body (250) o-rings (252) thus preventing fluid communication through transverse openings (232) to venting channels (256). FIG. 13B depicts a non-venting state that corresponds to an open state of cutter (60). As can be best seen in FIG. 7B, the open state of cutter (60) corresponds to cutter (60) being disposed in its furthest proximal position relative to lateral aperture (150). In the open state of cutter (60), there is no fluid communication of atmospheric air through first lumen portion (160). In other words, spool body (250) seals first lumen portion (160) relative to atmosphere at this stage. Thus, when a vacuum is applied to cutter (60), tissue may be prolapsed through lateral aperture (150).

FIG. 13C depicts spool body (250) in an intermediate non-venting state. In the present example, spool body (250) has two o-rings (252) separated by a distance corresponding approximately to the longitudinal length of lateral aperture (150) of cannula (120). Because of the separation between o-rings (252), and because spool body (250) translates with cutter (60), spool body (250) remains in a non-venting state as cutter (60) translates between its furthest proximal position to its furthest distal position relative to lateral aperture (150). In particular, FIG. 13C shows the spool body (250) in a position nearing a transition from non-venting to venting states. FIG. 7C depicts the corresponding position of cutter (60) when spool body (250) is in the position depicted in FIG. 13C. It should be understood that the distance between spool body (250) o-rings (252) may be of any suitable distance. Indeed, this distance may be less if it is desirable to vent to atmosphere when cutter (60) is in a more proximal position relative to lateral aperture (150). Alternatively, needle portion (110) may be of a different configuration necessitating a different distance such that the transition between a non-venting state and a venting state remains the same relative to cutter (60) position. Other configurations involving a different distance between spool body (250) o-rings (252) will be apparent to one of ordinary skill in the art in view of the teachings herein.

Figure 14:
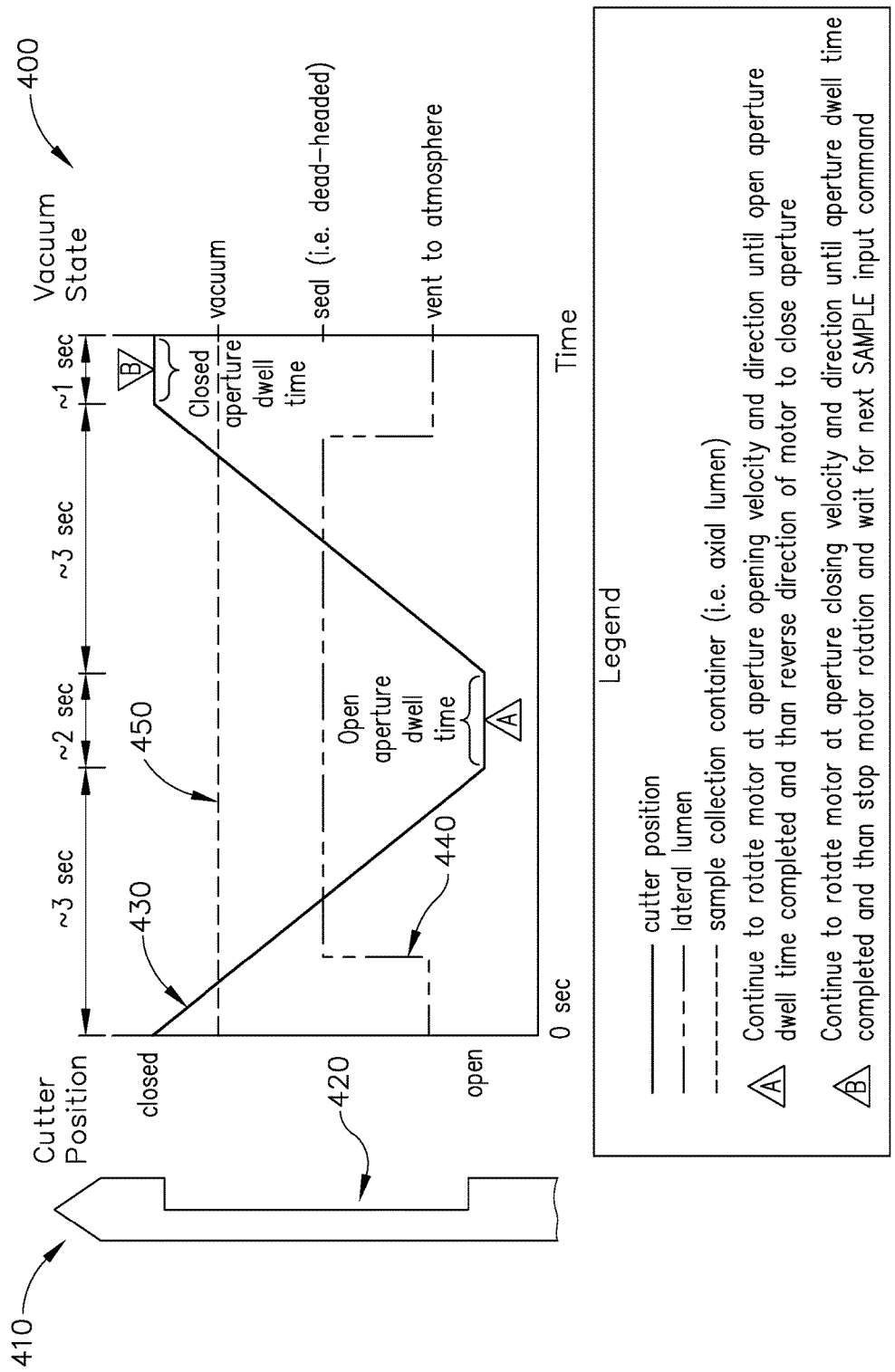
FIG. 14 depicts a graph showing the relationship between valve state and cutter position.

FIG. 14 depicts an exemplary pneumatic algorithm (400) that may be carried out during the use of biopsy device (10). In particular, FIG. 14 shows movements of cutter (60) in relation to cannula (120), which is represented by graphical representation (410) including a graphical representation (420) of lateral aperture (150). Movement of cutter (60) is shown in line (430) for a full range of travel for cutter (60). Line (440) represents pneumatic states of valve assembly (200) during the tissue extraction process; thereby indicating the pneumatic states of first lumen portion (160). The pneumatic state of second lumen portion (162) inside cutter (60) is shown by line (450). As can be seen, vacuum is applied to second lumen portion (162) constantly throughout the tissue extraction process. The term "dead head" in FIG. 14 is intended to mean that the corresponding first lumen portion (160) is sealed relative to atmosphere, and that vacuum is not permitted to freely flow from second lumen portion (162) to first lumen portion (160) during that stage.

As shown in FIG. 14, cutter (60) begins in the closed position which is shown in FIG. 7A. In this position, line (440) of FIG. 14 shows that valve assembly (200) is vented to atmosphere and line (450) shows second lumen portion (162) having a vacuum applied thereto. The corresponding position of valve assembly (200) can be seen in FIG. 13A.

As cutter (60) translates proximally from a closed state toward an open state, as shown by line (430) of FIG. 14 and as depicted in FIG. 7C, line (440) shows that valve assembly (200) correspondingly shifts to a "dead head" state where first lumen portion (160) is sealed to atmosphere. This transition with respect to valve assembly (200) is best seen in FIG. 13C. In the present example, this transition occurs when cutter (60) is located at a position to lateral aperture (150) where lateral aperture (150) is effectively approximately 24% open. However, it should be understood, that such a transition may occur at other cutter (60) positions relative to lateral aperture (150).

Once cutter (60) reaches an open position, as depicted in FIG. 7B, line (430) in FIG. 14 shows that cutter (60) may remain open for an open aperture dwell time (460). During open aperture dwell time (460), first lumen portion (160) is sealed relative to atmosphere. The corresponding position of valve assembly (200) is best seen in FIG. 13B. However, as indicated by line (450) a vacuum remains applied to second lumen portion (162) inside cutter (60). Thus, vacuum may travel through lateral aperture (150) via second lumen portion (162) such that tissue may be prolapsed through lateral aperture (150). In some examples, pneumatic algorithm (400) may include continued rotation of motor (70) at the same velocity as when cutter (60) was being opened. In such examples, motor (70) may be decoupled from a cutter drivetrain for the duration of open aperture dwell time (460). Yet, motor (70) may remain coupled to vacuum pump (50) to supply vacuum as indicated by line (450).

Line (430) of FIG. 14 next depicts cutter (60) shifting distally from an open position toward a closed position as shown in FIG. 7C. As cutter (60) translates distally, severing the prolapsed tissue, line (440) of FIG. 14 shows vent assembly (200) shifting from a dead head state to a venting state. This transition, with respect to vent assembly (200), is just after the state shown in FIG. 13C. As described above, this transition occurs when cutter (60) is located at a position to lateral aperture (150) where lateral aperture (150) is effectively approximately 13% open. However, it should likewise be understood that this position may be varied in other versions.

Finally, line (430) of FIG. 14 shows cutter (60) back in a closed position, as depicted in FIG. 7A, where it will remain for a closed aperture dwell time (470). In this state, line (440) of FIG. 14 depicts valve assembly (200) in a venting state as is shown in FIG. 13A. Thus, first lumen (160) may vent to atmosphere to create a pressure differential suitable for proximal movement of a severed tissue sample through cutter (60) and into tissue sample holder (40). As similarly described above with respect to open aperture dwell time (460), closed aperture dwell time (470) may include continued rotation of motor (70). However, unlike with open aperture dwell time (460), motor (70) may continue to rotate at the same velocity as when cutter (60) was being closed. It should be understood that during such rotation of motor (70), motor (70) may be decoupled from the cutter drivetrain for the duration of closed aperture dwell time (470). However, motor (70) may remain coupled to vacuum pump (50) to supply vacuum as indicated by line (450). Once closed aperture dwell time (470) has expired, the process described above may then be repeated as necessary to obtain the desired number of tissue samples. Of course, the various states described above are merely exemplary and other relationships between cutter (60) position, vent state, and vacuum will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, comprising:
   (a) a body;
   (b) a needle extending distally relative to the body, wherein the needle defines a first lumen and a second lumen, wherein the first lumen extends along a first longitudinal axis, wherein the second lumen extends along a second longitudinal axis, wherein the needle includes an opening fluidly coupling the first lumen with the second lumen;
   (c) a cutter, wherein the cutter is configured to translate relative to the needle to sever tissue; and
   (d) a valve assembly, the valve assembly including:
      (i) a vent opening, and
      (ii) a spool body including a plurality of vent channels extending through at least a portion of the spool body such that the plurality of vent channels are configured to communicate fluid from a proximal end portion of the spool body to a distal end portion of the spool body, wherein the spool body is movable relative to the vent opening between a first position and a second position, wherein the valve assembly is configured to couple the second lumen of the needle to the vent opening via at least one vent channel of the plurality of vent channels when the spool body is in the first position, wherein the valve assembly is configured such that the second lumen is sealed relative to the vent opening when the spool body is in the second position, wherein the spool body is coaxially disposed about the cutter.

2. The biopsy device of claim 1, wherein the needle further defines a transverse tissue receiving aperture, wherein the transverse tissue receiving aperture opens into the first lumen, wherein the cutter is operable to sever tissue protruding through the tissue receiving aperture.

3. The biopsy device of claim 1, wherein the cutter is configured to translate along the first longitudinal axis.

4. The biopsy device of claim 3, wherein the cutter is positioned in the first lumen.

5. The biopsy device of claim 3, wherein the spool body is movable along the first axis relative to the vent opening.

6. The biopsy device of claim 5, wherein the spool body is coupled to the cutter such that translation of the cutter directly corresponds to movement of the spool body along the first axis.

7. The biopsy device of claim 6, wherein the cutter is translatable between a first position and a second position, wherein the first position of the cutter corresponds to the spool body being in the first position, wherein the second position of the cutter corresponds to the spool body being in the second position.

8. The biopsy device of claim 7, wherein the cutter is configured to be fully advanced distally relative to the needle when the cutter is in the first position, wherein the cutter is configured to be fully advanced proximally relative to the needle when the cutter is in the second position.

9. The biopsy device of claim 1, wherein the valve assembly further includes a manifold, wherein the vent opening is defined by the manifold.

10. The biopsy device of claim 9, wherein the manifold is fixedly secured to the distal end of the body, wherein the manifold extends proximally from a distal end of the body.

11. The biopsy device of claim 10, wherein the needle extends distally from the manifold, wherein the needle is fluidly sealed relative to the manifold.

12. The biopsy device of claim 11, wherein the spool body is disposed within the manifold, wherein the spool body is slidable within the manifold relative to the vent opening.

13. The biopsy device of claim 12, wherein the distal and proximal end portions of the spool body each include a seal, wherein the seal is operable to create a fluid seal between an interior surface of the manifold and an exterior surface of the spool body.

14. The biopsy device of claim 13, wherein the seals on the distal and proximal end portions of the spool body include rubber o-rings.

15. A biopsy device, comprising:
   (a) a body;
   (b) a needle extending distally relative to the body, wherein the needle defines a first lumen and a second lumen, wherein the second lumen is offset from the first lumen, wherein the needle includes an opening fluidly coupling the first lumen with the second lumen;
   (c) a cutter, wherein the cutter is movable relative to the needle to sever tissue; and
   (d) a valve assembly, the valve assembly including:
      (i) a vent opening, and
      (ii) a valve member including a plurality of cutter engaging walls and a plurality of venting channels defined by at least a portion of one or more cutter engaging walls of the plurality of cutter engaging walls, wherein the valve member is configured to translate relative to the vent opening in response to translation of the cutter to selectively couple and decouple the vent opening with the second lumen of the needle via the venting channels.

16. The biopsy device of claim 15, further comprising a manifold extending proximally from a distal end of the body, wherein the needle is positioned coaxially relative to the manifold such that the needle extends distally from the manifold, wherein the vent opening is defined by the manifold.

17. The biopsy device of claim 16, wherein the valve member is disposed within the manifold, wherein the valve member includes at least two seals that are configured to seal between an interior of the manifold and an exterior of the valve member, wherein the valve member is slidable within the manifold such that the seals are movable relative to the vent opening between a first position and a second position.

18. The biopsy device of claim 17, wherein the vent opening positioned between the seals of the valve member when the seals are in the first position, wherein the vent opening is positioned proximally of the seals when the seals are in the second position.

19. A biopsy device, comprising:
(a) a body;
(b) a needle extending distally relative to the body, wherein the needle defines a first lumen and a second lumen, wherein the first lumen extends along a first longitudinal axis, wherein the second lumen extends along a second longitudinal axis, wherein the needle includes an opening fluidly coupling the first lumen with the second lumen;
(c) a cutter, wherein the cutter is configured to translate relative to the needle to sever tissue;
(d) a manifold, wherein the manifold defines a vent opening, and
(e) a spool body disposed on the cutter, wherein at least a portion of the spool body defines a plurality of venting channels extending axially relative to the cutter between an interior surface of the spool body and the cutter, wherein the spool body is translatable within the manifold relative to the vent opening to selectively couple and decouple the vent opening with the second lumen of the needle via the plurality of venting channels.

* * * * *